United States Patent [19]

Hammarström et al.

[11] Patent Number: 5,071,958

[45] Date of Patent: Dec. 10, 1991

[54] COMPOSITION INDUCING A BINDING

[75] Inventors: Lars Hammarström, Frejavägen; Leif Blomlöf, Krokusvägen; Sven Lindskog, Myrstuguvägen, all of Sweden

[73] Assignee: Bioventures N.V., Curacao, Netherlands

[21] Appl. No.: 581,031

[22] Filed: Sep. 12, 1990

Related U.S. Application Data

[62] Division of Ser. No. 321,680, Mar. 10, 1989, abandoned.

[30] Foreign Application Priority Data

Mar. 17, 1988 [SE] Sweden .............................. 8800980

[51] Int. Cl.$^5$ .......................... A61K 6/00; A61K 7/26; A61C 13/23
[52] U.S. Cl. .................................... 530/344; 514/21; 530/425; 433/226; 433/228.1; 604/54
[58] Field of Search ........................ 433/226, 228.1; 530/344, 425; 514/21; 604/54

[56] References Cited

U.S. PATENT DOCUMENTS 4,672,032  6/1987  Slavkin et al. .................. 435/68
4,702,734 10/1987  Terranova et al. ............... 604/54

OTHER PUBLICATIONS

Sasaki et al. "Biosynthesis of Enamel Matrix Components in Vitro and in Vivo".

*Primary Examiner*—John Doll
*Assistant Examiner*—Choon P. Koh
*Attorney, Agent, or Firm*—Brumbaugh, Graves, Donohue & Raymond

[57] ABSTRACT

A composition for use in inducing binding between parts of mineralized tissue by regeneration of mineralized tissue on at least one of the parts, containing as an active constituent a protein fraction originating from a precursor to dental enamel, so called enamel matrix;

a process for inducing binding between parts of living mineralized tissue by regeneration of mineralized tissue on at least one of the parts using such composition.

11 Claims, 1 Drawing Sheet

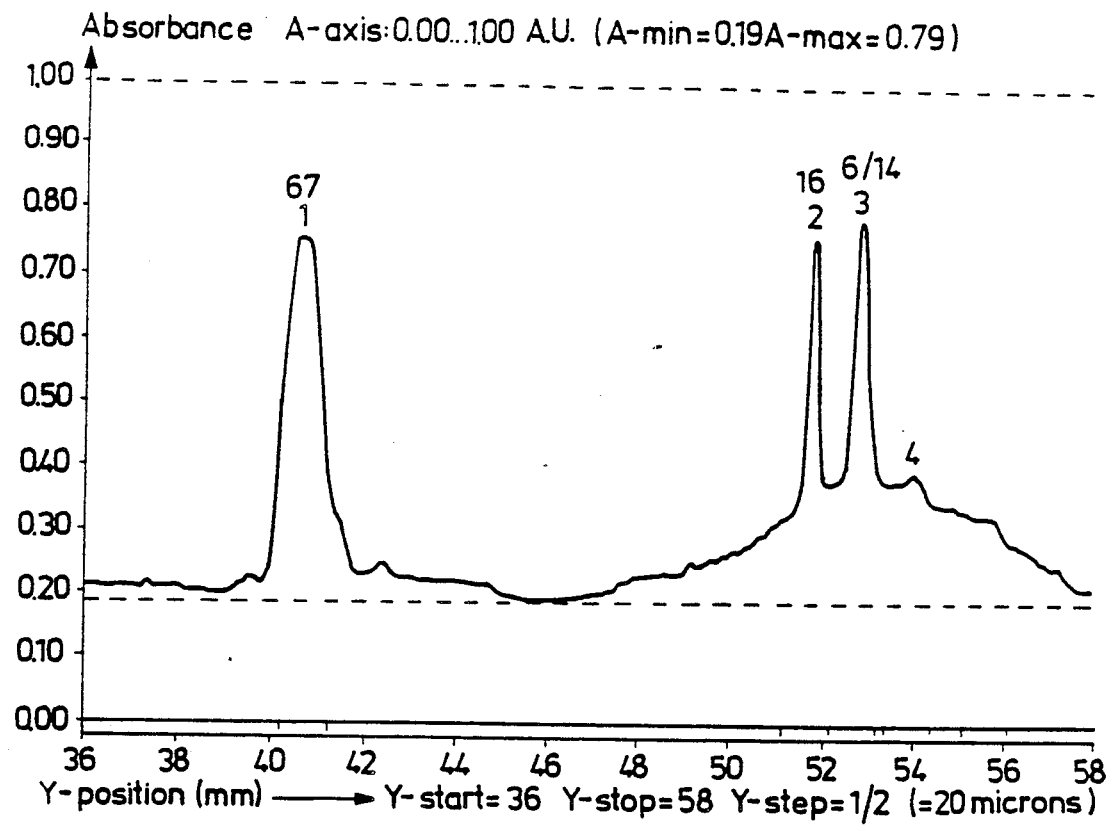
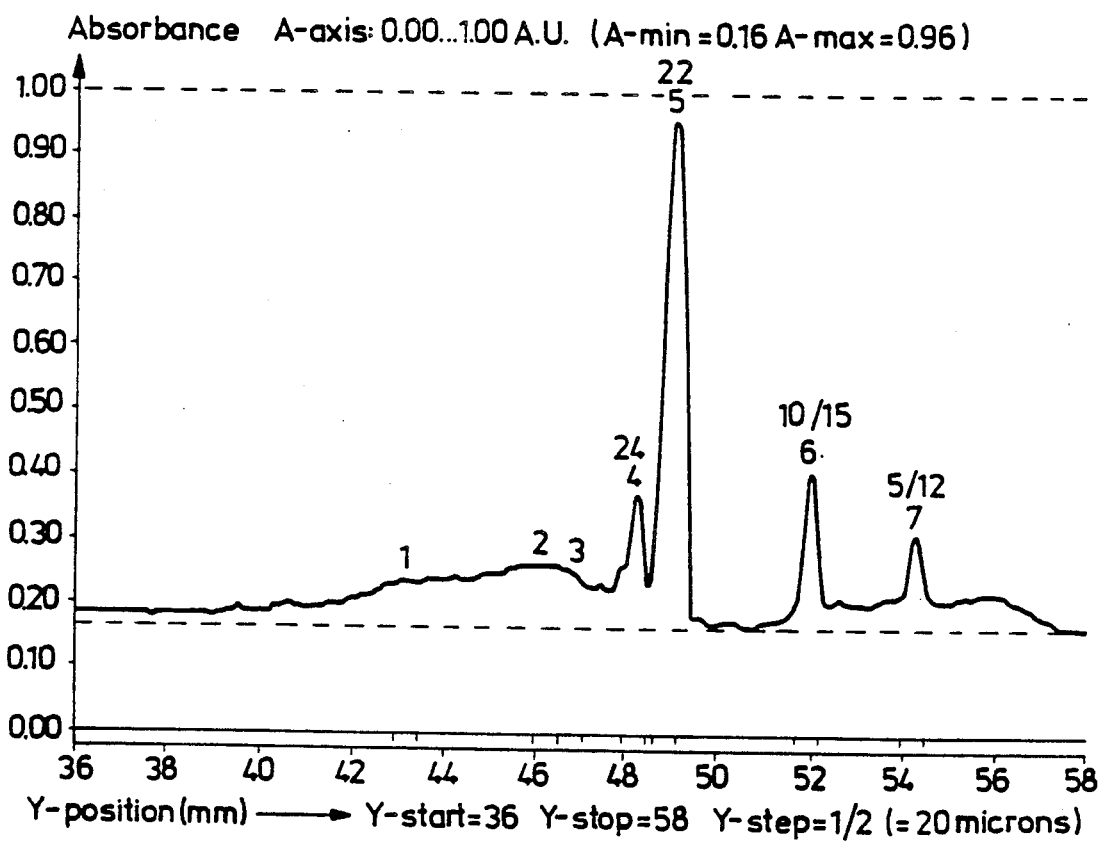

COMPOSITION INDUCING A BINDING

This application is a division of application Ser. No. 07/321,680, filed on Mar. 10, 1989 now abandoned.

BACKGROUND OF THE INVENTION

The present invention relates to a composition for use in inducing binding between parts of mineralized tissue by new formation of mineralized tissue on at least one of the parts but possibly also on the other part. The invention also relates to a process for inducing such binding, for example for the treatment of periodontitis.

The present invention relates to new biologically based techniques useful with regard to inducing binding between parts of mineralized tissue, for example teeth and bone. Even if the invention is generally applicable to provide for such binding it will, in the present disclosure, be illustrated mainly in connection with the treatment of loosening teeth, so called periodontitis. However, it should be noted that this principal illustration of the invention must not be interpreted in a limiting manner. Before the techniques of the invention are described more closely it is suitable, in order to facilitate understanding of the invention, to give a brief background to the biological conditions in connection with teeth and associated disorders. At normal dental status the teeth are anchored in special cavities, so called alveoli, in the jaw bone. Between the roots of the teeth and the jaw bone a so called periodontal membrane is located. The roots of the teeth are mainly constituted by a material called dentin. This dentin is peripherally covered by a thin layer of cementum, thickness about 0.01 to 1 mm. In this cementum inter alia collagen fibres are found which extend from the cementum through the periodontal membrane and which are anchored in the jaw bone. Thus, the cementum is extremely important for the attachment of a tooth to the jaw bone. The periodontal membrane has a thickness of about 0.2 mm and consists of the above-mentioned collagen fibres and vessels and nerves lying between said fibres and cells belonging to these tissues.

The jaw bone does not extend all the way up to the crown of the tooth, and in the part of the root which is not covered by jaw bone fibres from the root cementum extend out into the surrounding tooth gum, the gingiva. These fibres assist in anchoring the tooth and, furthermore, stabilize the tooth gum. The tooth gum, as well as the whole oral cavity, is covered by a thin layer of epithelium. This epithelium forms a dense collar or sleeve around the teeth. Adjacent to the teeth there is formed a shallow furrow between the teeth and the epithelium.

Inflammatory disorders in the tissues attaching the teeth to the jaw bone are quite frequent and strike to a varying extent the major part of the population all over the world. The methods of treatment hitherto used are mainly aiming at retarding an ongoing disease process and at preventing loosening of the teeth as far as possible. Presently, no clinically useful method exists that provides healing in such a manner as to enable the teeth to regain attachment to the jaw bone.

A further problem within this area of inflammatory disorders is constituted by congenital defects in dental attachment. Patients with such defects develop symptoms of periodontitis at an early age, so called juvenile periodontitis. Its treatment often involves extraction of the tooth and replacement with some bridge construction at a substantial cost.

The bacteria on the surface of the teeth cause chronic inflammation in the tooth gum around the teeth. Inflammatory cells excrete their enzymes intended to kill the bacteria, but which in this case also attach the collagen fibres attaching the tooth to gingiva and jaw bone. The cells on the surface of the tooth root or the cementum thus become subject to destruction, and epithelium from the oral mucous membrane grows downwardly along the teeth and produces a so called gingival crevice. In this crevice new bacteria encounter favourable growth conditions and new inflammatory cells invade this area making the decomposition of the tissues of the periodontal membrane to proceed. The cementum cells die and the bone of the alveolar area is destroyed. The process generally is a very slow one but may at intervals proceed very fast. After some time the teeth subject to attack will completely lose their attachment to the jaw bone.

Today's treatment is principally directed at removing the bacterial deposits on the tooth surfaces. When the bacteria are removed the inflammation of the gingiva and the periodontal membrane ceases and the decomposition process comes to a stop. That treatment also aims at preventing new bacterial deposits to form on the dental surface. It thus results in stopping the destruction of the attachment of the teeth to the jaw bone, but now new periodontal membrane or new cementum will be formed in the healing process.

SUMMARY OF THE INVENTION

In connection with the research of which the present invention is a result, use has been made of the knowledge that the formation of cementum is initiated by a thin layer of a precursor to enamel which, in development of the root is formed along all of the root surface. It should be noted that it is not public knowledge that the precursor to enamel can induce formation of cementum. This knowledge, however, is described in co-pending patent applications, such as European patent application No. 87850264.0. Further research and experiments on the mechanism for the formation of cementum have surprisingly revealed that the precursor to dental enamel, so called enamel matrix, contains as an active constituent a protein fraction obtainable from the organic part of said enamel matrix. This discovery is all the more surprising since the biological function of the proteins constituting said protein fraction is believed to reside in the formation and particularly mineralization of dental enamel (cf. Fischer, L. & Termine, D, Clinical Orthopaedics 200, 1985, 362-85). The proteins of enamel matrix are composed of a high molecular weight part and a low molecular weight part, and it has been found that their active constituent is constituted by the low molecular weight part of same but may also be constituted by an active determinant thereof. Said low molecular weight part of the enamel matrix proteins is constituted by acetic acid extractable proteins generally referred to as amelogenine which have a molecular weight of up to about 40.000, but mainly a molecular weight within the range of about 5000 to about 25000.

DETAILED DESCRIPTION OF THE INVENTION

With regard to the expressions "precursor to enamel" and "enamel matrix" as used herein reference is made to two references wherein the meaning of said expressions is made fully clear, namely:

A. R. Ten Cate, Oral Histology, Development, Structure, and Function, The C. V. Mosby Co., St. Louis, USA (1980) pp 182-83.

I. A. Mjör, O. Fejerskov, Human Oral Embryology & Histology, Munksgaard, Copenhagen (1986) pp 44-45.

The full disclosures of these references are incorporated herein by reference.

In connection with the present invention, it has been found that if dentin is exposed to the cells of the periodontal membrane, for example by grinding a cavity in the surface of the root, healing takes place in the form of a bone-like tissue lacking the fibres which attach the healthy tooth to surrounding tissues. If, however, the artificially generated cavity surface is covered with an active protein fraction originating from a precursor to dental enamel, which precursor to dental enamel in the following is called enamel matrix, it is found that normal cementum anchoring tissue is generated.

The enamel matrix proteins are obtained preferably from a mammal, such as a bovine or porcine species. In the experiments it has been found that one can induce formation of cementum in monkeys and humans by covering a cavity ground in the surface of the root with a protein fraction obtained from enamel matrix from another species, such as for example a porcine species.

Thus, the invention described in the following provides for new techniques for inducing binding between parts of living mineralized tissue by fresh formation of mineralized tissue on at least one of the parts. These techniques are characterized by the application of enamel matrix proteins originating from a precursor to dental enamel, so called enamel matrix, for the induction of binding. Thus, the invention further provides for a composition for such use, said composition containing as an active constituent such enamel matrix proteins or an active determinant.

As previously indicated, the invention is particularly applicable in connection with dental therapies, for example in the treatment of periodontitis, i.e. loosening of teeth, in transplantation of teeth or in reintroduction of teeth disconnected by accident. However, the invention can also be used to facilitate attachment of artificial implants, for example tooth implants or artificial hip joints. The invention may also be used to induce formation of mineralized tissue on artificial implants where it is desired to provide for a new tendon attachment.

The protein fraction used in applying the techniques according to the present invention is suitably obtained from the enamel matrix of some mammal, the teeth of which are under development. A suitable source of the enamel matrix are slaughtered animals, for example pigs or calves, the slaughter of which often takes place while the teeth still are under development, in the case of pigs often at an age of about half a year. Preferred mammals are thus selected from bovine or porcine species (i.e. cattle or pigs) but also other species are conceivable, for example sheep and rodents which have continuously growing teeth. As an alternative source of this protein fraction one may also use cultivated cells or bacteria modified by recombinant DNA-techniques, cf., for example, U.S. Pat. No. 4,672,032.

The composition to be used for therapy according to the invention may consist of only such protein fraction or an active determinant thereof, suitably admixed with water, but the composition may also contain the protein fraction in combination with a carrier, diluent or adhesive, such as modified celluloses, agar, alginate or gelatin acceptable for the purpose. For dental use it is suitable that the carrier or diluent is dentally acceptable. It is presently preferred to use a carrier comprising water soluble polymers. Examples of such polymers but without restriction thereto are sodium carboxycellulose, microcrystalline cellulose, hydroxyethylcellulose, hydroxypropylcellulose, methylcellulose, high molecular weight polyacrylic acid, sodium alginate, propyleneglycol alginate, xanthan gums, guar gum, locust bean gum, modified starch, gelatin, pectin or combinations of these. After incorporation of the active protein fraction these water soluble polymers may, optionally, be converted to gels or films resulting in compositions that are easily applied due to their advantageous physical properties. The composition may optionally contain stabilizers or preserving agents for the purpose of increasing storage stability.

The invention also provides a process for the treatment of periodontitis involving regaining attachment of the teeth by inducing a formation of root cementum and jaw bone and a physiological collagen fibre attachment between these. The process is characterized in that epithelium, if present, is removed from the root of the tooth and the root is then supplied with a layer of the relevant protein fraction obtained from enamel matrix.

In the preferred application of the invention for the treatment of periodontitis the collagen tissue (gingiva) adjacent to area of a tooth subject to attack is incised to expose the surface of the root. Epithelium, if present, is removed and the clean surface of the root is then coated with a layer of said protein fraction or a composition containing such protein fraction as an active constituent, after which the collagen tissue (gingiva) is repositioned and optionally sutured so that healing can take place.

As previously mentioned the invention can be used, in addition to the treatment of periodontitis, in reimplantation or transplantation of teeth. It is relatively frequently occurring that youths in their lower teens have accidents resulting in dislocation of one or several teeth, mainly front teeth. By quickly putting back the dislocated teeth good healing can be obtained with normal attachment to the jaw bone. In many cases such reinstatement of dislocated teeth cannot be carried out immediately and the teeth must be kept for a period of time in an unsuitable medium outside the mouth, for example in the air. This will destroy the cells of the periodontal membrane on the surface of the root. When the tooth is put back in location in the mouth it will not regain a physiological attachment but will eventually loosen. Up to now no method has been devised by which one can obtain permanent tooth attachment through connecting tissue regeneration.

In accordance with the techniques of the invention the dead periodontal membrane on the dislocated tooth may, however, be removed in a suitable manner by mechanical or chemical means, and the composition containing or consisting of said protein fraction is then applied to the naked surface of the root. The tooth is then put back into its alveolus and lightly fixed for some weeks. Due to the protein fraction or composition thereof applied on to the surface of the root a new cementum layer will be generated and the tooth will hereby obtain new attachment.

In regard to the transplantation of teeth, i.e. transfer of teeth from one individual to another, it has been found that the tissues of transplanted teeth are attacked by the immune defense of the receiver and decomposed in a very short period of time. Attempts have been made to carry out transplantation between immunologically compatible individuals. Also the results of these attempts have, however, been discouraging. Since long-term treatment with immuno suppressants for the purpose of maintaining one or several transplanted teeth is not worth the risks coming with it there is today no clinically useful method for transplantation of teeth with a favourable long-term prognosis.

However, by employing the techniques according to the present invention such as method can be devised and the problem can be solved by removing the teeth to be transplanted from the donor, removing the dental pulp, cleaning the pulp space and applying a root filler agent in the pulp space. The periodontal membrane is mechanically or chemically removed and the root of the tooth is covered with the composition containing the active protein fraction. Then the tooth is placed in its new location in the receiver's mouth. The tooth is maintained in a fixed position for a period of time, and due to the protein fraction, reformation of endogeneous mineralized tissue which covers the transplanted tooth and provides fixation of same will be induced.

According to a further preferred aspect of this invention the composition containing the active protein fraction may be supplemented with a tissue adhesive based on fibrinogen, Factor XIII (which is a plasma-derived coagulation factor) and thrombin. Such supplemented composition may be constituted by a premix of enamel matrix and fibrinogen and Factor XIII, the thrombin being added immediately before applying the composition to the surgical site. The premix may optionally contain aprotinin to reduce the rate of decomposition. A useful commercial product for use in such supplemented composition is Tiesseel a two-component fibrin sealant manufactured and sold by IMMUNO AG, Vienna, Austria. In using such tissue adhesive the premix of protein fraction, fibrinogen, Factor XIII and, optionally, aprotinin, is mixed with a thrombin solution, and the resulting composition is then rapidly applied to the surgical site. In the treatment of periodontitis this technique greatly facilitates surgery. Thus, the adhesion of the composition to the root is enhanced, bleeding is stopped and positioning of the muco-periosteal flap is greatly simplified while eliminating the use of sutures.

Presently preferred products for use in a supplemented composition according to the invention are cellulose derivatives and alginates, such as carboxymethyl celluloses and sodium or propylene glycol alginate.

The invention will in the following be further illustrated in conjunction with specific examples. The exemplification is made in connection with dental experiments performed on monkeys and humans. In this exemplification reference is made to the appended drawing which represents a SDS-Page, polyacrylamide gel electrophoresis separation. The two main parts of the protein fraction obtained from enamel matrix based on molecular weight are called amelogenin (low molecular weight) and enamelin (high molecular weight).

EXAMPLE 1

Preparation of Extracts for Animal Tests.

For establishing which components in enamel matrix that are active in the animal models, the following test substances were prepared. All substances originate from porcine enamel matrix.

E 1—0.3 g of matrix (protein contents 27+4%) were slurried in 3 ml of 0.9% NaCl and homogenized under cooling with ice with a Polythrone for 1 minute at intervals of 10 seconds. The homogenate was then freeze dried. Yield: 199 mg, protein content according to Lowry 47%+2%.

E 2—0.3 g of matrix were slurried and homogenized as above and then heated on water bath for 4 minutes. Freeze drying gave a yield of 199 mg, contents of soluble protein 13%+3%.

E 3—0.3 g of substance were slurried in 3 ml 0.5M acetic acid (p.a.), homogenized as above and were then allowed to stand under stirring at 4° C. for 24 hours for protein extraction. Then, centrifugation in the cold was made to 10.000 rpm for 10 minutes. The precipitate was recovered and frozen, and the supernatant was freeze dried. Yield of lyophilisate: 68 mg, protein content 29%+3%.

E 4—0.3 g of matrix were slurried in 3 ml 10% EDTA in 0.03M Tris buffer, pH 7.4, and homogenized under cooling as above. Then extraction took place by stirring in the cold for 24 hours, the homogenate being then centrifuged off in a cooling centrifuge. The supernatant was dialized against distilled water and freeze dried. Yield: 11 mg, protein contents 33%+2%.

E 5—The precipitate after centrifugation (E 4) was extracted with about 10 volumes of 0.5M acetic acid under slow stirring in the cold for 24 hours. Then a new centrifugation was performed and the supernatant was freeze dried. Yield: 109 mg, protein contents 15%+3%.

E 6—The precipitate from centrifugation described under E 5 was freeze dried. Yield: 37 mg, protein contents 18%+4%.

E 7—0.3 g of matrix were slurried in 3 ml 10% EDTA in 0.03M Tris buffer, pH 7.4, with 0.4 mM proteinase inhibitor PMSF (phenyl methyl sulfonyl fluoride) and homogenized and extracted in the same manner as sample E 4. After centrifugation and dialysis of the supernatant freeze drying took place. Yield: 11 mg, protein content 41%+2%.

E 8—The precipitate from the centrifugation described under

E 7—was extracted with 0.5M acetic acid for 48 hours at a low temperature, centrifuged and the supernatant was freeze dried. Yield: 101 mg, protein contents 17%+1%.

E 9—The precipitate from centrifugation described under E 8 was freeze dried. Yield: 40 mg, protein contents 30%+3%.

The substances obtained in E 1-9 above were characterized with regard to protein content, protein molecular weight distribution (SDS-Page with Phast), isoelectric points of the proteins and carbohydrate content.

Apparent molecular weight compositions of extracts from porcine enamel matrix are shown in the appended drawing. After SDS-polyacrylamide gel elektrophoresis (SDS 8-25%, Phast, Pharmacia) the protein bands have been transformed to peaks by a laser scanner (LKB Ultroscan XL). Molecular weights are estimated from calibration with protein (14-90 kDa) and polypeptide (2-14 kDa) references (Pharmacia. Diagrams are given for extracts E4 and E5 and these and the other abstracts are summarized below.

| Extract | Protein components (SDS-Page molecular weights) | | | | | | |
|---|---|---|---|---|---|---|---|
| No | about 5/12* | 6/14* | 10/15* | 16 | 22 | 24 | 67 kDa |
| E1 | x | x | x | x | X | x | X |
| E3 | x | x | x |   | X | (x) |   |
| E4 |   | x |   | x |   |   | X |
| E5 | x |   | x |   | X | (x) |   |
| E7 |   | x |   | x |   |   | X |
| E8 | x |   | x |   | X | (x) |   |

*The lower molecular weights are obtained when the polypeptide calibration kit is used and the higher molecular weights when the protein calibration kit is used.
X = large amount, x = small amount, (x) = minor amount.

The purpose of this example is to show the influence of substances E 1-E 9 obtained by step-wise extraction from the precursor tissue to dental enamel (enamel matrix) on healing of experimentally produced marginal periodontal wounds. Defects in the marginal periodontium of monkey teeth were created by removing dental cementum, periodontal membrane and marginal alveolar bone to a cervico-apical distance of approximately 5 mm with a dental bur. The substances were then applied to the experimentally produced defects and the wound was allowed to heal. Control defects were also prepared but allowed to heal without the application of any substance. After a healing period of 8 weeks the results were evaluated histomorphometrically.

The results of the healing process are expressed in percent of the original level of cementum and bone cover (Table 1). The healing process comprises the formation of an adhering layer of new cementum, periodontal membrane and alveolar bone (new attachment).

TABLE 1

| Substance | Control | E1 | E2 | E3 | E4 | E5 | E6 | E7 | E8 | E9 |
|---|---|---|---|---|---|---|---|---|---|---|
| Healing (%) | 5 | 93 | 3 | 79 | 4 | 49 | 2 | 0 | 48 | 5 |

Thus, attachment had resulted after the application of substances E1, E3, E5 and E8. This was not the case for the control and teeth treated with substances E2, E4, E6, E7 and E9 where the defect persisted whereas the teeth had only been covered with oral epithelium. These results indicate that the application of the low-molecular weight fraction of the protein part of enamel matrix promotes tissue attachment in the treatment of periodontitis.

EXAMPLE 2

Preparation of Desalted Acid Extract From Enamel Matrix.

A freeze dried preparation similar to that of the preceding example (E 3) was dissolved in 0.1M acetic acid and transferred (144 mg/12 ml) onto a 15×540 mm column with Sephadex G-25 superfine in 0.1M acetic acid. The first protein-rich fraction (E10) was collected and freeze dried. The yield was 34 mg of material containing about 72% protein which corresponds to 85% of proteins in starting material. Residual proteins were found in the salt fraction (63 mg of freeze dried material having a protein content of about 7%.

The freeze dried protein fraction prepared in this manner was filled into 10 ml vials (20 mg in each) and irradiation sterilized (35 kGy) before use in animal testing.

The preparations were analyzed as described in the preceding example. Results are given in Table 2 below.

TABLE 2

| Substance | Control | E10 |
|---|---|---|
| Healing (%) | 4 | 72 |

EXAMPLE 3

Preparation of purified protein fractions 200 mg of freeze dried preparation E3 (identical to the one used in Example 2) was dissolved in 20 ml 0.1M acetic acid and applied to a 25×780 mm column with Sephadex G-75 in 0.1M acetic acid at 4° C. The column was eluted at a rate of 55 ml/h and 4 ml samples were collected. The eluate was monitored red at 280 nm (Uvicord) and the samples containing the major part of eluted material were combined to yield five fractions which were analyzed by electrophoresis (SDS-Page) for molecular weight distribution as shown below. Five peaks from the elution chromatogram (0-1 A)

Fraction Sample
(1) 50–60: high molecular weight proteins, "enamalins" (MW>40,000)
(2) 62–80: high molecular weight amelogenin (MW about 25 kilo daltons)
(3) 90–100: intermediate molecular weight amelogenin (MW about 14 kilo daltons)
(4) 110–125: low molecular weight amelogenin (MW about 5–10 kilo daltons)
(5) 130–160: salts After freeze-drying peaks (2), (3) and (4) yielded 10 mg, 7 mg and 12 mg of the high MW, intermediate MW and low MW amelogenin proteins respectively (protein content>90%).

The purpose of this experiment was to show the influence of Amelogenin substances of high, intermediate and low molecular weight extracted from the precursor tissue to enamel (enamel matrix) on healing of experimental marginal periodontal wounds. Experimental defects in the marginal periodontium of monkey teeth were created by removing dental cementum, periodontal membrane and marginal alveolar bone to a cervicoapical distance of approximately 5 mm with a dental bur. The substances were then applied to the experimentally produced defects and the wounds allowed to heal. Control defects were also prepared but allowed to heal without the application of any substance. After a healing period of 8 weeks the results were evaluated histomorphometrically (Table 3)

TABLE 3

| Substance | Control | Amelogenin: | | |
|---|---|---|---|---|
|  |  | High-MW | Intermediate-MW | Low-MW |
| Healing (%) | 4 | 78 | 21 | 15 |

Thus, new attachment had resulted after the application of high molecular weight amelogenin and, to a lesser degree, following application of intermediate molecular weight amelogenin and low molecular weight amelogenin. These results indicate that an application of the high-molecular weight fraction of the amelogenin obtained from enamel matrix most efficiently promotes tissue attachment in the treatment of periodontitis.

EXAMPLE 4

Preparation of Acid Extract of Enamel Matrix

Lower jaws from slaughtered pigs (about 6 months of age, slaughter weight about 80 kg) were cut free from soft tissue and frozen at the slaughter house. Suitable tooth germs were excised from frozen jaw halves after partial thawing, and enamel matrix was isolated.

38 g of enamel matrix were slurried in 780 ml 0.5M acetic acid, pH 4.1, and homogenized under ice cooling (Homogenisator Polytron PT 10-30). The homogenate was stirred in the cold for 22 hours to extract protein soluble at pH about 4. Unsoluble material was centrifuged away and the acetic acid solution was freeze dried.

8.5 g of lyophilisate were obtained having a protein content of about 20% corresponding to about 50% protein yield.

The freeze dried extract was analyzed with regard to water content, acetate content, protein content (Lowry), carbohydrate content (Antron reagent), aminoacid composition, elementary analysis, protein molecular weight distribution (SDS-Page) and isoelectric points of the proteins.

Before use in clinical testing the protein-containing acetic acid solution was sterile-filtered down into sterile 10 ml vials and freeze dried under sterile conditions.

The purpose of this example was to show the influence of substance E 3 on healing when treating marginal periodontitis in man. After approval from the Swedish Medical Board and The Regional Ethics Comittee the composition was used as an adjunct to conventional surgical treatment of patients with marginal periodontitis. The patients were operated to remove dental calculus and granulation tissue. The substance E3 was "painted" on the naked root surfaces and covered with a muco-periostal flap. The healing results were evaluated by periodical clinical inspection, recording of pocket depth, attachment level and gingival index as well as examination of intra-oral radiographs. The results were compared with those obtained in earlier quantitative studies using conventional periodontal surgery and similar control areas in the same patients.

The results showed that substance E3 had promoted a significant increase of marginal alveolar bone height (range 4–8 mm) and attachment level (range 5–9 mm). This was a healing result never seen after conventional periodontal surgery. Healing in general, appeared to progress more rapidly both regarding clinical appearance and reduction of marginal pocket depths compared with previous studies on conventional periodontal surgery. These results show that the low-molecular weight protein fraction from enamel matrix has the ability to promote new periodontal tissue attachment in man, a result not seen with conventional treatments.

TABLE 4

Analyses of enamel matrix homogenate and protein fractions obtained from enamel matrix homogenate.

| Analysis | Enamel matrix homogenate (E1) | Acid extract (E3) | Desalted extract (E10) | Salt fraction (Example 2) |
|---|---|---|---|---|
| Elementary Analysis (% w/w) | | | | |
| C | 11.3 | 31 | 50.4 | ND |
| H | 1.7 | 4.4 | 6.8 | ND |
| N | 3.9 | 4.5 | 15.5 | 0.7 |
| O | 9.4 | 27.5 | 21 | ND |
| S | 0.2 | 0.35 | 1.3 | 0.1 |
| Cl | 5.5 | 0.6 | <0.1 | 1.3 |
| P | 8.8 | 3.5 | 0.1 | 4.3 |
| Ca | 11.9 | 12 | <0.1 | 31.6 |
| K | 0.2 | 0.4 | <0.1 | ND |
| Protein content (% w/w) | | | | |
| Lowry analysis | 23 | 20 | 72 | <4 |
| Aminoacid analysis | <23 | <26 | <90 | ND |
| Carbohydrate content (% w/w) | | | | |
| Antron reagent | ND | 0.4 | 1.3 | ND |
| Water content (% w/w) | | | | |
| Karl Fischer titration | ND | 2 | 6 | ND |
| Acetate content (% w/w) | | | | |
| GC-method | ND | 38 | 4 | ND |
| Amino acid analysis (residue % w/w of total residues) | | | | |
| Pro | ND | 18.0 | 19.0 | ND |
| Glu | " | 17.8 | 19.0 | " |
| Leu | " | 9.0 | 9.1 | " |
| His | " | 8.7 | 9.2 | " |
| Ser | " | 4.8 | 4.6 | " |
| Gly | " | 3.2 | 2.8 | " |
| Tyr | " | 6.4 | 5.3 | " |
| Thr | " | 3.6 | 3.4 | " |
| Val | " | 3.6 | 3.5 | " |
| Met | " | 4.3 | 5.3 | " |
| Ile | " | 3.5 | 3.6 | " |
| Asp | " | 3.6 | 3.0 | " |
| Phe | " | 3.8 | 3.7 | " |
| Ala | " | 1.6 | 1.5 | " |
| Lys | " | 2.5 | 1.8 | " |
| Arg | " | 3.0 | 2.5 | " |
| Trp | " | 2.6 | 2.5 | " |
| Cys | " | 0 | 0 | " |

Improvement of Bone Healing

The effect "the low molecular weight part of the protein fraction of enamel matrix" of bone healing was tested on experimental cavities in the mandibles and the femurs of adult rats. The angular parts of the mandibles were exposed through a vertical surgical incision in the skin and the maseter muscle. A small hole (2 mm in diameter) was drilled through the mandibular bone under constant flow of physiological saline. In the same way holes of the same size as in the mandibles were prepared through the compact bone in the distal part of the femoral bones. In the right mandibles and the right femoral bones "the low molecular weight part of the protein fraction of enamel matrix" was applied while the holes in the left mandibles and the left femoral bones were used to control cavities.

"The low molecular weight part of the protein fraction of enamel matrix" was applied in the cavities either as a freeze-dried sponge-like material or small gelatine cylinders. Control holes in the mandibles and femoral bones on the left side of these rats were filled with gelatin cylinders without "the low molecular weight part of the protein fraction of enamel matrix". Nothing was applied in the control holes in the mandibles and the femoral bone on the left side of the rats given the dry, freeze-dried "the low molecular weight part of the protein fraction of enamel matrix".

The rats were killed 1-5 weeks after the application of the substances. The experimental and control areas were removed, and prepared for light microscopic examination.

As early as one week after the application of the low molecular weight part of the protein fraction of enamel matrix in the drilled hole it was completely filled with bone and, in addition, a marked periosteal apposition of bone had taken place. In the control not treated in accordance with this invention new bone had also been formed, but it was markedly less and the drilled hole had not healed.

We claim:

1. A process for bonding a piece of living mineralized tissue to a bonding site on a piece of other living tissue by regeneration of mineralized tissue at a bonding site on the piece of living mineralized tissue, comprising the steps of
   (a) removing any soft tissue present from the bonding site of the piece of living mineralized tissue,
   (b) applying to the bonding site on the piece of living mineralized tissue or to the bonding site on the piece other living tissue a layer of a composition comprising a low molecular weight protein fraction of enamel matrix that is effective to promote bonding, and
   (c) joining the bonding sites of the piece of living mineralized tissue and the other living tissue whereby the bonding sites are bonded together by regeneration of mineralized tissue.

2. A process according to claim 1, wherein the piece of living mineralized tissue is a tooth and the piece of other living tissue is soft gingival tissue and wherein the step of removing any soft tissue present is performed by exposing the surface of the root and removing any epithelium present, the composition is applied by coating the exposed surface of the root with said composition, and the joining of bonding sites is accomplished by repositioning the soft gingival tissue over the coating of the composition and optionally stitching the soft tissue so as to facilitate healing.

3. A process according to claim 1, wherein the enamel matrix is isolated from a mammalian source.

4. A process according to claim 3, wherein said enamel matrix is isolated from a bovine or porcine source.

5. A process according to claim 1, wherein the protein fraction is obtained by means of recombinant DNA-techniques or cultivation of diploid cells.

6. A process for preparing a composition for use in inducing bonding between a piece of living mineralized tissue and a piece of other living tissue by regeneration of mineralized tissue comprising the steps of
   (a) isolating tooth germs from mammalian jaws;
   (b) freeing said germs from enamel organ,
   (c) recovering enamel matrix from said freed germs,
   (d) homogenizing the enamel matrix,
   (e) separating a low molecular weight protein fraction from the homogenized enamel matrix, said protein fraction being effective to promote bonding by regeneration of mineralized tissue, and
   (f) optionally mixing the protein fraction with a carrier, diluent or adhesive.

7. A process according to claim 6, wherein the isolation is made from a bovine or porcine source.

8. A process according to claim 6 or 7, wherein said carrier, diluent or adhesive is dentally or biologically acceptable.

9. A process according to claim 1, wherein the piece of other living tissue is also living mineralized material.

10. A process according to claim 1, wherein the piece of living mineralized material is a tooth.

11. A process according to claim 1, wherein said protein fraction is obtained by acetic acid extraction of enamel matrix.

* * * * *